United States Patent [19]

Currie

[11] Patent Number: 5,178,537
[45] Date of Patent: Jan. 12, 1993

[54] DENTAL INSTRUMENT

[76] Inventor: Peter E. Currie, 504 Maitland Street, London, Ontario, Canada, N6B 2Z6

[21] Appl. No.: 482,783

[22] Filed: Feb. 21, 1990

Related U.S. Application Data

[63] Continuation-in-part of Ser. No. 267,099, Nov. 4, 1988, abandoned.

[51] Int. Cl.⁵ .............................................. A61C 19/04
[52] U.S. Cl. ...................................... 433/72; 433/146; 433/147
[58] Field of Search ................ 433/72, 141, 146, 147, 433/75; 206/369, 370, 375

[56] References Cited

U.S. PATENT DOCUMENTS

| | | | |
|---|---|---|---|
| 3,759,375 | 9/1973 | Nappi | 206/370 |
| 3,935,640 | 2/1976 | Cohan | 32/40 R |
| 3,943,914 | 3/1976 | Grenfell et al. | 128/2 S |
| 4,011,658 | 3/1977 | Jarrson et al. | 433/216 |
| 4,109,384 | 8/1978 | Dorian | 433/147 |
| 4,364,730 | 12/1982 | Axelsson | 433/72 |
| 4,445,857 | 5/1984 | Borst | 433/75 |
| 4,501,555 | 2/1985 | Ditchburn | 433/29 |
| 4,552,531 | 11/1985 | Martin | 433/147 |
| 4,768,952 | 9/1988 | Loewenthal | 433/72 |
| 4,886,454 | 12/1988 | Lowenthal et al. | 433/72 |
| 4,995,403 | 2/1991 | Beckman et al. | 433/72 |

FOREIGN PATENT DOCUMENTS

| | | | |
|---|---|---|---|
| 1044 | 3/1979 | European Pat. Off. | 433/147 |
| 8804159 | 6/1988 | PCT Int'l Appl. | 433/72 |
| 8905117 | 6/1989 | PCT Int'l Appl. | 433/72 |

OTHER PUBLICATIONS

Article Entitled "Microscopic Evaluation of Clinical Measurements of Connective Tissue Attachment Levels".
Hu-Friedy Catalogue.

Primary Examiner—Cary E. O'Connor
Attorney, Agent, or Firm—Krass & Young

[57] ABSTRACT

A periodontal probe tip for attachment to an elongate handle includes a disposable, non-metallic probe tip device having a measuring tine with markings thereon for measurement. The tip device includes a smooth, cylindrical connecting shaft to which the handle can be detachachably attached for use of the probe. The tip device is preferably made from strong, flexible nylon such as nylon 6. The preferred measuring tine has color bands for measuring distances. The preferred bands are 2 to 3 mm across. The probe tips can be individually packaged and sterilized in a package having a paperboard backer and a transparent plastics cover sealingly attached to the backer.

16 Claims, 4 Drawing Sheets

DENTAL INSTRUMENT

This application is a continuation-in-part of my co-pending U.S. patent application Ser. No. 267,099 filed Nov. 4, 1988, now abandoned.

BACKGROUND OF THE INVENTION

This invention relates to periodontal probes used by dentists to determine the size of periodontal pockets formed around teeth.

The use of periodontal probes in dentistry is well known. These instruments are employed to measure and map the size of periodontal pockets around the teeth of patients. The measurements are required to determine the extent of gum disease. The commonly employed probes have a metal measuring tine with suitable markings thereon to enable the dentist to measure the depth from the visible gum line of the tooth to the bottom of the periodontal pocket. The measuring tine is connected to a suitable elongate handle. These known devices can be sterilized in the usual manner, such as by use of an autoclave.

One concern that dentists have and that their patients have at this time is the risk of possible infection or disease being passed through instruments from one patient to another. Metal instruments such as the known periodontal probes which have a fairly fine point could possibly infect a dentist when it is being used through inadvertence or accident. It will be appreciated that these probes are being inserted into a patient's mouth in areas where infection and germs can reside and their tips can come into contact with a patient's infected blood, for example. If the dentist should accidently stab himself with the probe end, any infection that the patient has can easily be passed on to him. The dentist is thus in greater danger than another patient since the instrument would, in the normal course, be disinfected after each use.

However dental patients have a legitimate concern that the known probes have been properly disinfected before they are inserted into their own mouths. Since some infections, such as acquired immune deficiency syndrome, are deadly, this concern is legitimate and cannot be ignored by dentists. It is felt that one way of overcoming this concern by patients would be to have a periodontal probe with a probe tip that will only be used once and then disposed of. This way the patient can be assured that there is no risk of an infection or disease being passed to him.

Another problem with the known metal periodontal probes is that the metal probe tip can cause discomfort to the patient. Because the probe tip is quite small and therefore somewhat sharp, it can cause pain to the patient unless used with utmost care. The pain caused by the metal tip is increased by the fact that the probe tip is fairly rigid like a needle and therefore has no give when the tip is placed against the bottom of the periodontal pocket.

A further difficulty of the known periodontal probes is that the marking lines on the measuring tine can be quite hard to see, particularly when the tine is in the mouth of a patient. It is of course important that the periodontal pocket be measured correctly for an accurate diagnosis. Because of the size of a probe tip, it is difficult, if not impossible, to put numerical markings on the tip and therefore some other method must be used to indicate the measurement clearly to the dentist who is using the probe.

It is an object of the present invention to provide a disposable periodontal probe tip having a flexible measuring tine with markings thereon for measurement and an integral connecting shaft to enable the tip to be detachably attached to a handle.

It is a further object of the present invention to provide a disposable probe tip device that can be readily attached to a suitable handle in an easy manner and in a manner which will not pass infections or germs to the sterilized probe tip.

SUMMARY OF THE INVENTION

According to one aspect of the invention, a periodontal probe tip for attachment to a probe handle includes a disposable, non-metallic probe tip device having a strong, flexible measuring tine with markings thereon for easy measurement. The device also has a integral connecting shaft adapted to rigidly and detachably attach the device to the handle for use of the probe. The device is made of strong, flexible plastics material. The measuring tine has a circular cross-section along its length.

Preferably the tip device is made of flexible nylon.

According to another aspect of the invention, a periodontal probe includes a elongate handle and a disposable, flexible plastics probe tip having a measuring tine with markings thereon for measurement. The probe tip includes an integral connecting shaft to which the handle is detachably attached by insertion of the shaft into a threaded opening in one end of the handle. The shaft has a smooth, cylindrical peripheral and is held in the handle by the combination of an interference fit with the interior of the handle and engagement by the threads in the opening.

There is also described herein a packaged dental probe tip including sterilized, disposable, flexible plastics probe tip device having a strong, flexible measuring tine with markings thereon for measurement. The tip device also has an integral connecting shaft to which a handle can be detachably attached. A package completely encloses the probe tip device separately from any other probe tip device.

Further features and advantages will become apparent from the following detailed description when taken in conjunction with the accompanying drawings.

DETAILED DESCRIPTION OF PREFERRED EMBODIMENT

Figure 1:
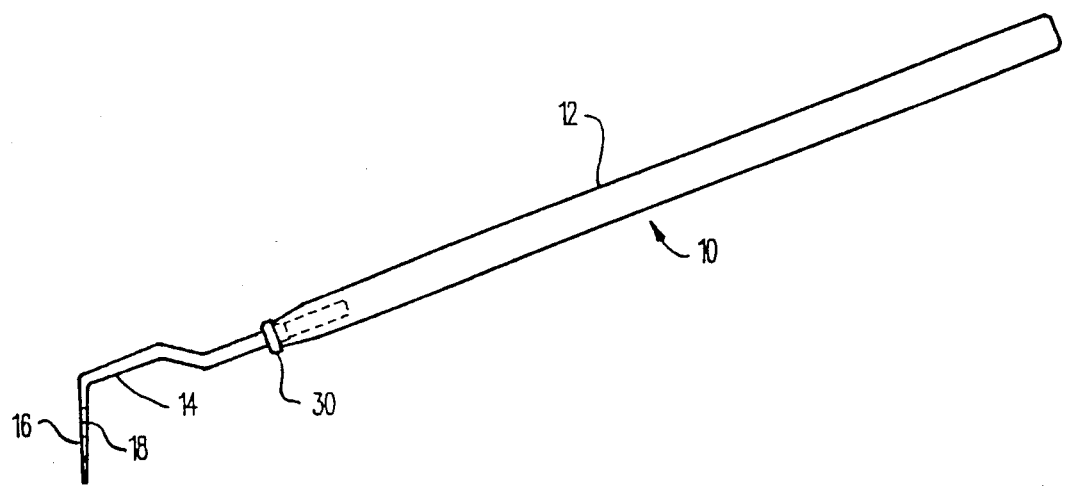
FIG. 1 is a side view of a periodontal probe constructed in accordance with the invention, which view shows the approximate actual size of the probe.

In FIG. 1 there is shown a periodontal probe 10 for use by a dentist in the measurement of periodontal pockets around a patient's teeth. The probe includes an elongate, rigid handle 12 which is preferably made of stainless steel. This handle can have suitable ridges or grooves formed thereon (not shown) for ease of manipulation. It can be of standard construction and therefore suitable for other purposes such as a dental mirror handle. At the bottom end of the handle 12 is a probe tip 14 constructed in accordance with the invention. This tip is made of an inexpensive non-metallic material, namely a flexible plastics material, so that it can be disposed of after use on a single patient. As in known probe tips, the tip 14 has a measuring tine 16 with markings 18 thereon for measurement.

Figure 2:
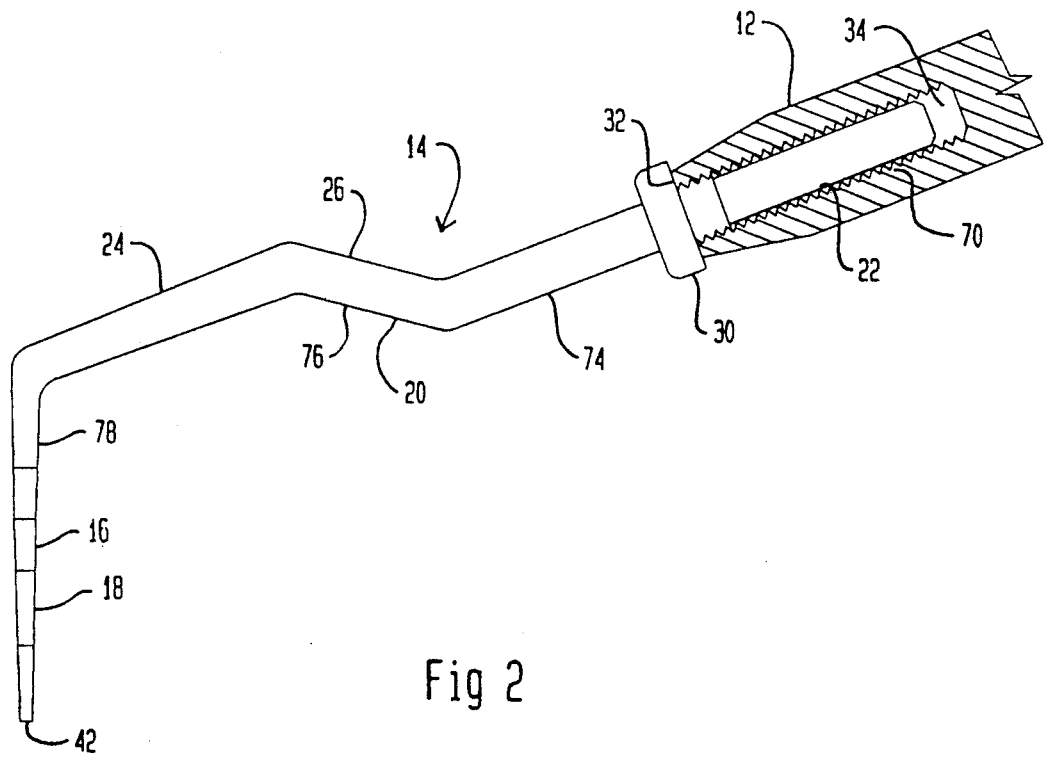
FIG. 2 is a detailed view of the probe tip showing the end of the probe handle in axial cross-section.

Details of the preferred probe tip 14 can be seen from FIG. 2. The probe tip can be divided into three sections including the aforementioned measuring tine 16, an intermediate section 20 extending from an upper end of the tine and integrally connected thereto, and a connecting shaft 22 to which the handle 12 can be detachably attached for use of the probe. The shaft is integrally connected to one end of the intermediate section 20. The intermediate section 20 in the preferred embodiment includes a first portion 24 which extends at an obtuse angle to the measuring tine 16 and a shorter second portion 26 that extends at an obtuse angle to the first portion 24 and is an integral extension thereof. This second portion 26 extends at an obtuse angle to the connecting shaft 22. It will be appreciated that the shape of the intermediate section 20 and its disposition relative to the measuring tine permits a probe constructed in accordance with the invention to be easily manipulated over and around teeth. In a preferred embodiment the length of the first portion 24 is 11.5 mm while the length of the second portion 26 is 6.5 mm.

Preferably the connecting shaft 22 is provided with a collar 30 which, when the probe tip is properly and fully inserted into the handle 12 engages or rests against one end 32 of the handle. The collar 30 provides means for the dentist to insert the probe shaft and ensures that the shaft is not inserted too far into the handle but is inserted a sufficient distance to provide for a secure attachment. The shaft is inserted into a threaded opening 34 formed in the end of the handle.

The material from which the probe tip is made is important as it must be sufficiently strong that a portion of a tip will not break off during use of a probe. It could cause a hazard to a patient if the tip broke off in his mouth. It is also desirable that the probe tip be flexible to some extent so that it will not cause undue discomfort to a patient when it is being used by a dentist. A suitable plastics material can be selected for the probe tip.

Of course because the probe tip is meant to be disposable, the material should be relatively inexpensive. One preferred material is nylon 6 which has a density of 1.1 and a tensile strength of 11.5 ksi. It can have a bright yellow colour and can provide a smooth surface. It has a modulus of elasticity up to 400 ksi and it will not support the growth of fungi. There is of course the possibility of a patient biting the probe tip during use thereof by the dentist and, for this reason also, the tip must be strong. Another preferred plastics material which is less flexible than Nylon 6 is glass fiber filled nylon such as the 33% glass fiber filled nylon sold by Dupont under the trade name Zytel 70 G 33L. Another usable nylon is 13% glass fiber filled nylon sold under the trade name Zytel 70 G 13L.

Figure 3:
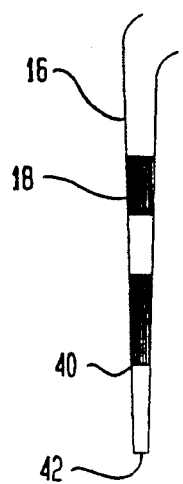
FIG. 3 is a detailed view showing the preferred markings on the probe tip.

A preferred form of the markings 18 on the probe tip is illustrated in FIG. 3. In particular the tine 16 is marked with colour bands for measuring distances, the first band being 3 mm across and the second being 2 mm across. These bands could, for example, be made light blue in colour which provides a good contrast to the bright yellow of the remaining portions of the probe tip. As illustrated in FIG. 3, the bottom of a first blue band is located at 40 which is 3 mm from the probe end 42. The top of the first blue band is separated by 2 mm from the second blue band. With a little practice, it is relatively easy for a dentist to determine the depth of a periodontal pocket with a measuring tine marked in this manner. The paint used to mark the probe tip should be non-toxic, quick drying, and permanent to nylon if nylon is used. Preferably the edges of the coloured bands should be formed on the tine 16 by tiny V-grooves about 0.1 mm deep. The paint for the bands can be florescent if desired to improve readability. As an alternative, the plastics material itself can be made florescent. The color bands can be applied by a two color pad printer. A full 360 degrees coverage of the tip can be achieved by printing one side, then rotating the tip in a jig and printing a second time.

Figure 4:
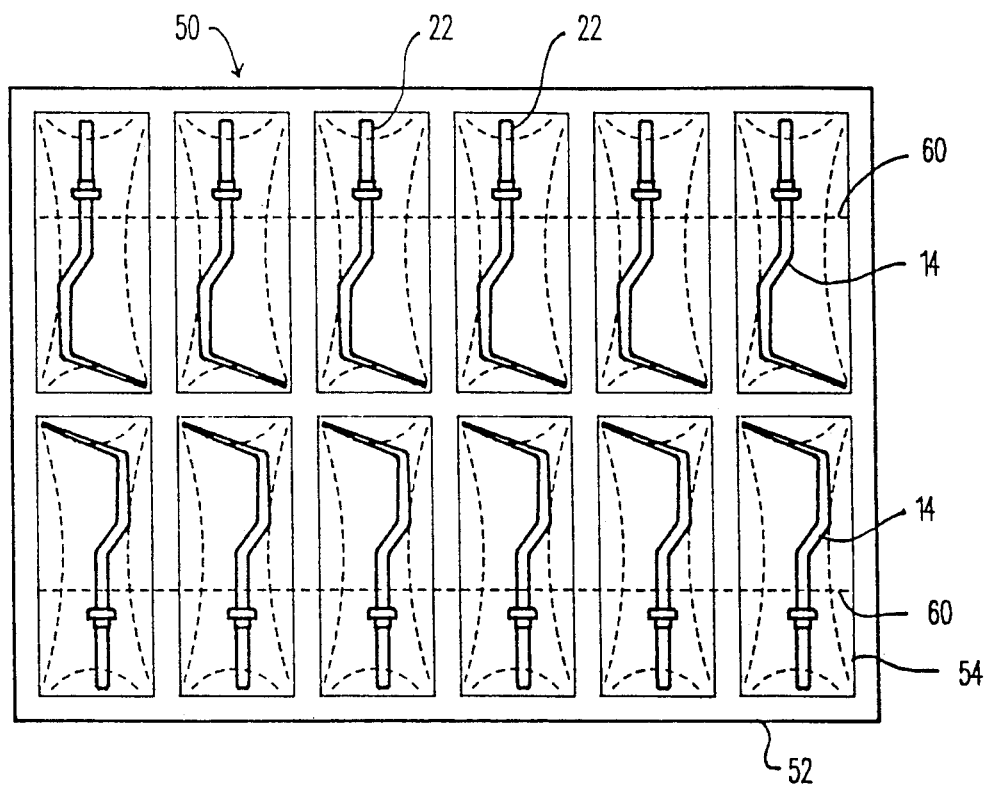
FIG. 4 is a plan view of a blister package having compartments for a number of disposable probe tips constructed in accordance with the invention.
Figure 5:
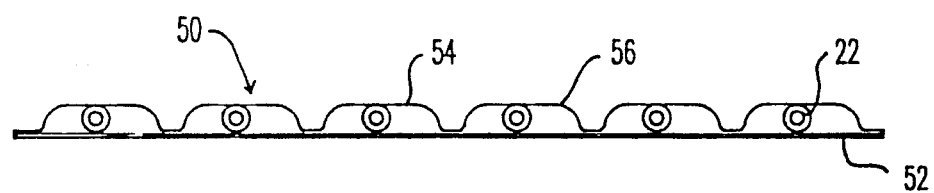
FIG. 5 is an edge view of the package of FIG. 4.
Figure 6:
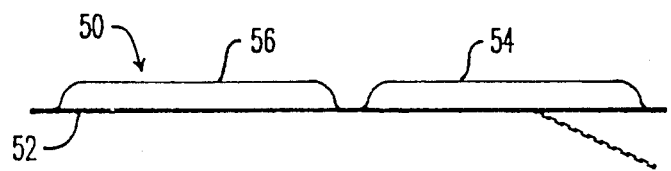
FIG. 6 is another edge view of the package taken from the righthand side of FIG. 4.

The disposable probe tips 14 of the invention can be provided in a sterile manner by the use of a package such as that shown in FIGS. 4 to 6. In this package 50 the individual probe tips 14 are completely separated from one another. The package includes a backer 52 and a transparent, plastics cover 54 sealingly attached to the backer in a known manner. The preferred material for the backer 52 is a plastics material but paperboard or cardboard could be used. The cover 54 forms a number or pockets or bubbles 56 arranged in rows and sized to accommodate the probe tips. The probe tips can be removed one at a time by exposing the connecting shaft 22 and pushing on the metal handle 12 so as to form a fiction fit.

The illustrated package is provided with lines of perforations 60. These lines permit the cardboard backer 52 to be partially ripped back as illustrated in FIG. 6, thereby exposing the aforementioned connecting shaft 22. After the package has been completely emptied of its probe tips, it can simply be thrown out.

As explained, one form of fixing the probe tip in the handle is to push the connecting shaft 22 or stem into the opening 34 of the steel handle. The stem or shaft 22 is slightly oversized in order to achieve an interference fit. In addition to this the final 1.5 mm of the engagement (before the collar 30 rests against the handle end) is accomplished by a twist action on the part of the user. This action causes the screw threads 70 to tap into the nylon material and produce a positive fix of the probe tip. The collar 30 can be used by the dentist to accomplish this fixing and later can be used to disconnect the probe tip.

Sterilization of the packaged probe tips can be accomplished either by ethylene oxide gas or by gamma radiation. A gamma radiation dose of 1.0 to 1.5 Mrad has been found to be a good level for this purpose as it does not affect the nylon material.

The preferred angle of the tine 16 relative to the centre line of the connecting shaft 22, the handle 12, and the intermediate portion 24 is about 69 degrees. The shape of the probe tip provides for maximum clearance over the teeth while permitting the connecting shaft 22 to be aligned with the handle axis. The diameter of the probe tip is selected to ensure sufficient stiffness while not blocking the operator's view. In a preferred embodiment, the shaft section 74 has a diameter of 2 mm which is also the diameter at location 76 on intermediate section 20. The measuring tine 16 in this preferred embodiment tapers from a diameter of 1 mm at the location indicated by reference 78 to a width of only 0.5 mm at the tip 42.

Figure 7:
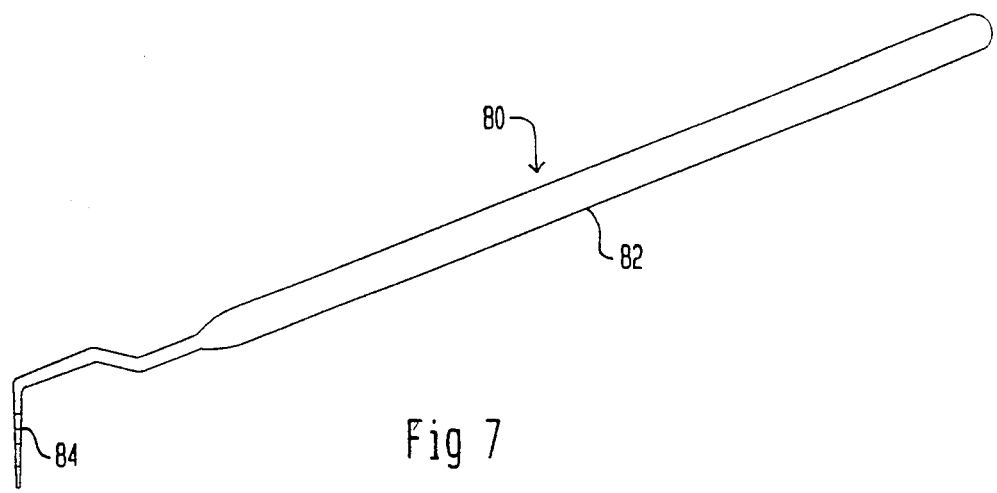
FIG. 7 is a side view of another embodiment of the invention wherein the probe tip is an integral extension of the probe handle.

FIG. 7 illustrates another embodiment wherein the entire periodontal probe including the handle is intended to be disposable. In this embodiment the probe 80 is made of plastics material such as a strong flexible nylon. In other words both the handle 82 and the probe tip 84 are made of plastics, the tip being an integral extension of the handle. This probe can be made by any suitable moulding process.

Figure 8:
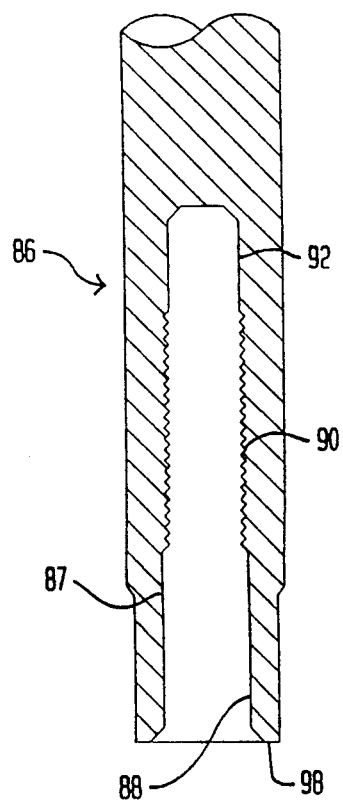
FIG. 8 is an axial cross-sectional detail of the connecting end of a preferred form of handle for the probe.

FIG. 8 of the drawings illustrates an alternative version of the connecting end of a handle for the periodontal probe. The connecting end 86 has an opening or passageway 87 extending along the central axis of the handle. The initial portion 88 of this passageway is unthreaded while a central portion of the passageway at 90 is threaded so as to provide a positive engagement with an inserted connecting shaft of a probe tip. In one version of the handle the threads are No. 3–48 in the central section. An innermost section 92 of the passageway is also unthreaded and has a diameter less than that of the section 88.

Figure 9:
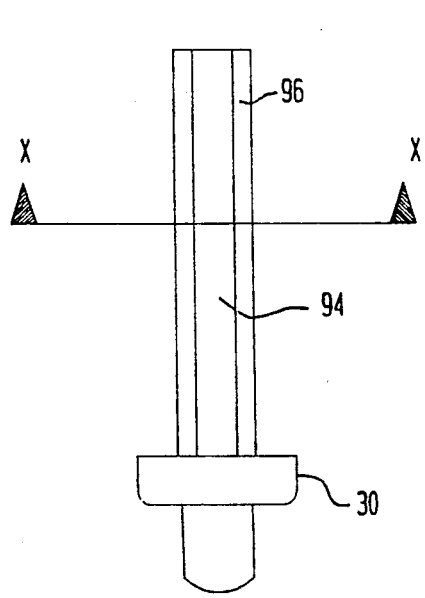
FIG. 9 is a side view of a preferred form of connecting shaft for the probe tip.
Figure 10:
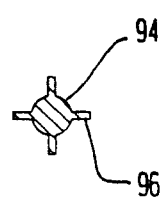
FIG. 10 is a cross-sectional view taken along the line X—X of FIG. 9.

A preferred form of connecting shaft for the probe tip is shown in FIGS. 9 and 10. This integral connecting shaft 94 has longitudinally extending ribs 96 extending the length of the shaft. In the illustrated version there are four of these ribs 96 arranged at 90 degree angles about the circumference of the shaft. In one preferred embodiment of this connecting shaft, the length of the shaft is 14 mm while the diameter of the shaft (not including ribs) is 1.4 mm. The maximum diameter of this particular shaft including the ribs is 2.7 mm. The width of each rib in this version is 0.25 mm. The connecting shaft is secured in the passageway 87 of the handle by pushing the shaft 94 all of the way into the passageway so that the collar 30 presses against the end 98 of the handle. The probe tip is then given a one quarter turn to fully engage the threads of the handle with the ribs 96.

Preferably the probe tips are molded in a mold that uses a sliding gate in order that the tip will be smooth, with no mold parting lines along the sides.

If desired, the paint or ink used to place the markings on the probe tip can be selected so as to choose a type that loses adhesion to the plastic or nylon if the probe tip is autoclaved or chemically sterilized. The advantage of such a selection is, of course, that the probe tip is unlikely to be used more than once. This helps avoid the possibility of a non-sterile probe tip being used inadvertently or by mistake.

Possible changes and modifications to the described disposable probe tip will be apparent to those skilled in this art after considering the above description and the accompanying drawings. Accordingly all such modifications and changes as fall within the scope of the appended claims are intended to be part of this invention.

I therefore claim:

1. A periodontal probe tip for attachment to a probe handle comprising a probe tip device having a strong, flexible measuring tine with markings thereon for measurement and an integral connecting shaft adapted to rigidly and detachably attach the device to said handle for use of the periodontal probe, said device being made of strong, flexible plastics material and said measuring tine having a circular cross section along its length.

2. A periodontal probe tip for attachment to a probe handle comprising a probe tip device having a strong, flexible measuring tine with markings thereon for measurement and an integral connecting shaft to which said handle can be detachably attached for use of the periodontal probe, said device being made substantially from a material selected from the group consisting of nylon 6 and glass fiber filled nylon.

3. A dental probe tip for attachment to a probe handle comprising a disposable probe tip device having a strong, flexible measuring tine with markings thereon for measurement a connecting shaft to which said handle can be detachably attached for use of the periodontal probe, said device including an intermediate section extending from an upper end of said tine and connected to said tine and said shaft, wherein said intermediate section includes a first portion extending at an obtuse angle to said measuring tine and a shorter second portion extending at an obtuse angle to said first portion and integrally connected thereto, said second portion extending at an obtuse angle to said connecting shaft.

4. A probe tip according to claim 3 wherein said tip device is made substantially of nylon 6.

5. A probe tip according to claim 4 wherein said measuring tine is marked with color bands for measuring distances, said bands being from 2 to 3 mm across.

6. A periodontal probe comprising an elongate handle, a disposable, flexible plastics probe tip having a measuring tine with markings thereon for measurement and an integral connecting shaft to which said handle is detachably attached by insertion of said shaft into a threaded opening in one end of said handle, wherein said shaft has a smooth, cylindrical periphery and is held in said handle by the combination of an interference fit with the interior of said handle and engagement by the threads in said opening.

7. A periodontal probe according to claim 6 wherein said probe tip is made of strong, flexible nylon.

8. A periodontal probe according to claim 7 wherein said shaft is formed with a collar which engages one end of said handle to assist in insertion of said shaft and to ensure that the shaft is inserted the proper distance into said opening.

9. A periodontal probe according to claim 7 wherein said measuring tine is marked with colour bands for measuring distances, said bands being from 2 to 3 mm across.

10. A periodontal probe according to claim 6 wherein said handle is made of metal.

11. A periodontal probe according to claim 6 wherein said connecting shaft is adapted to rigidly attach the probe tip to said handle.

12. A periodontal probe according to claim 11 wherein said measuring tine has a circular cross section.

13. A periodontal probe comprising an elongate handle and a plastics probe tip having a strong, flexible measuring tine with markings thereon for measurement and an integral connecting shaft to which said handle can be detachably attached by insertion of said shaft into an opening in one end of said handle.

14. A periodontal probe according to claim 12 wherein said handle is made of steel.

15. A periodontal probe according to claim 13, wherein said measuring has a circular cross section along its length and said connecting shaft rigidly attaches said probe tip to said handle.

16. A periodontal probe tip for attachment to a probe handle comprising a probe tip device made substantially of nylon and having a measuring tine with a circular cross section and markings thereon for measurement and a connecting shaft to which said handle can be detachably attached for use of said probe tip, said shaft being adapted to rigidly attach the probe tip device to said handle.

* * * * *